US006733534B2

(12) United States Patent
Sherman

(10) Patent No.: US 6,733,534 B2
(45) Date of Patent: May 11, 2004

(54) SYSTEM AND METHOD FOR SPINE SPACING

(75) Inventor: Michael C. Sherman, Memphis, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 10/059,496

(22) Filed: Jan. 29, 2002

(65) Prior Publication Data

US 2003/0144737 A1 Jul. 31, 2003

(51) Int. Cl.$^7$ .................................................. A61F 2/44
(52) U.S. Cl. .................................. 623/17.16; 623/17.11; 606/61
(58) Field of Search .......................... 623/17.11, 17.12, 623/17.13, 17.14, 17.15, 17.16, 23.65, 23.67, 23.68, 7, 8, 9; 606/192, 194, 61

(56) References Cited

U.S. PATENT DOCUMENTS

| 4,570,618 A | 2/1986 | Wu |
| 4,966,600 A | 10/1990 | Songer et al. |

(List continued on next page.)

FOREIGN PATENT DOCUMENTS

| EP | 0322334 | 6/1988 |
| WO | WO 94/01057 | 1/1994 |
| WO | WO 98/20939 | 5/1998 |
| WO | WO 98/56301 | 12/1998 |
| WO | WO 99/08616 | 2/1999 |
| WO | WO 99/29246 | 6/1999 |
| WO | WO 99/40866 | 8/1999 |
| WO | WO 01/28442 | 4/2001 |
| WO | WO 02/03882 | 1/2002 |
| WO | WO 02/17825 | 3/2002 |
| WO | WO 03/045262 | 4/2003 |

OTHER PUBLICATIONS

About Kyphon; Nov. 14, 2001; 2 pages; http://kyphon.com/us/main.cfm?action=about&page=kyphx.
Clinical Trial Evaluates New Surgical Option for Sufferers of Lower Back Pain; Maine Medical Center; Oct. 17, 2001; 2 pages; http://www.mmc.org/news/xstop.html.
X.STOP; St. Francis Medical Technnologies, Inc.; Oct. 24, 2001; 7 pages; http://www.sfmt.com/ipd1.html.
The X–Stop Implant; St. Mary's Medical Center; Oct. 17, 2001; 1 page; http://www.chwbay.org/index.py–screen=News&currNode=10259.htm.
Novel Treatments for Degenerative Spinal Discord; St. Francis Medical Technologies, Inc., Oct. 17, 2001; 1 page; http://www.sfmt.com/sfmthome.html.
St. Francis Medical Completes Enrollment in Pivotal FDA Clinical Study Of Prosthesis for Lumbar Spinal Stenosis; Oct. 17, 2001; 2 pages; Yahoo.

(List continued on next page.)

Primary Examiner—Cary E. O'Connor
Assistant Examiner—Candice C. Melson
(74) Attorney, Agent, or Firm—Coat & Bennett, P.L.L.C.

(57) ABSTRACT

A system and method for positioning a spacer within a patient. The device has a first form having a reduced size to be inserted into the patient in a minimally invasive manner. The device than expands to a second form once inside the patient to an enlarged size. In one embodiment, the expansion results from biomaterial fed into the device. In another embodiment, the expansion results from the device being constructed of an expandable material that enlarges after being inserted into the patient. The method includes forming a minimally invasive opening within the patient for delivering the device to an application point. In one embodiment, a conduit is positioned within the patient for delivering the device. The conduit may also be used to deliver biomaterial to the interior of the device.

30 Claims, 3 Drawing Sheets

U.S. PATENT DOCUMENTS

| | | |
|---|---|---|
| 4,969,888 A | 11/1990 | Scholten et al. |
| 5,011,484 A | 4/1991 | Breard |
| 5,092,866 A | 3/1992 | Breard et al. |
| 5,108,404 A | 4/1992 | Scholten et al. |
| 5,116,340 A | 5/1992 | Songer et al. |
| 5,496,318 A | 3/1996 | Howland et al. |
| 5,571,189 A * | 11/1996 | Kuslich .................. 623/17.12 |
| 5,609,634 A | 3/1997 | Voydeville |
| 5,645,599 A | 7/1997 | Samani |
| 5,725,582 A | 3/1998 | Bevan et al. |
| 5,827,289 A | 10/1998 | Reiley et al. |
| 5,836,948 A | 11/1998 | Zucherman et al. |
| 5,888,220 A | 3/1999 | Felt et al. |
| RE36,221 E | 6/1999 | Breard et al. |
| 6,017,305 A | 1/2000 | Bonutti |
| 6,042,596 A | 3/2000 | Bonutti |
| 6,066,154 A | 5/2000 | Reiley et al. |
| 6,074,390 A | 6/2000 | Zucherman et al. |
| 6,099,531 A | 8/2000 | Bonutti |
| 6,102,928 A | 8/2000 | Bonutti |
| 6,187,023 B1 | 2/2001 | Bonutti |
| 6,235,043 B1 | 5/2001 | Reiley et al. |
| 6,238,397 B1 | 5/2001 | Zucherman et al. |
| 6,336,930 B1 | 1/2002 | Stalcup et al. |
| 6,423,083 B2 | 7/2002 | Reiley et al. |
| 6,440,169 B1 | 8/2002 | Elberg et al. |
| 6,575,919 B1 | 6/2003 | Reiley et al. |
| 2003/0033017 A1 * | 2/2003 | Lotz et al. ............... 623/17.16 |

OTHER PUBLICATIONS

Spinal Stenosis; Oct. 17, 2001; 3 pages; http://www.spinal-stenosis.org/.

What is Spinal Stenosis; Oct. 17, 2001; 6 pages; http://www.spinalstenosis.org/ss1.html.

Spinestudy.org; Oct. 17, 2001; 5 pages; http://www.spine-study.org/.

Publ. No. 2002/0188299; Structures and Methods for Creating Cavities in Interior Body Regions; Reiley et al; Dec. 12, 2002; 21 pgs.

Publ. No. 2002/0082598; Percutaneous Vertebral Fusion System; Teitelbaum; Jun. 27, 2002; 25 pgs.

R.J. Minns, and W.K. Walsh; Preliminary Design and Experimental Studies of a Novel Soft Implant for Correcting Sagittal Plane Instability in the Lumbar Spine; 1997, Lippincott–Raven Publishers; SPINE vol. 22, No. 16, pp. 1819–1827.

Dispositif Inatervertebral Amortissant; Appendix B; 4 pgs.

* cited by examiner

SYSTEM AND METHOD FOR SPINE SPACING

BACKGROUND

A large majority of the population will experience back pain at some point in their lives that results from a spinal condition. The pain may range from general discomfort to disabling pain that immobilizes the individual. One type of adverse spinal condition is spinal stenosis which occurs when the spinal canal or nerve root canals become too narrow and reduces the space for the passage of blood vessels and nerves resulting in low back pain as well as pain in the legs. Spinal stenosis can result from the natural aging process, or may be a result of a degenerative disease or condition.

One method currently used for treating spinal stenosis is a decompressive laminectomy. This procedure requires that the patient be given a general anesthesia as an incision is made in the patient to access the point of injury and repair the damage. This procedure may result in blood loss, an increased chance of significant complications, and usually results in an extended hospital stay of two or more nights. This procedure is further complicated when the patient is elderly, which is often the case when treating spinal injuries of this type.

Medical treatments that can be performed in a minimally invasive manner are greatly sought after by the medical community and patients alike. The term "minimally invasive" herein shall be understood as being accomplished without the need to resect tissue in order to gain access to the application point. Minimally invasive techniques are advantageous because they can be performed with the use of a local anesthesia, have a shorter recovery period, result in little to no blood loss, and greatly decrease the chances of significant complications. Minimally invasive techniques additionally are usually less expensive for the patient.

SUMMARY

The present invention is a system and method of positioning a spacer within a patient. The spacer has a first form having a reduced size such that it can be inserted into the patient in a minimally invasive manner. Once inserted to an application point within the patient, the spacer is expanded to a desired size. In one embodiment, a conduit is placed within the patient to a predetermined position between adjacent spinous processes. The spacer is inserted in a first form through the conduit to the application point and then changed to the second form having an expanded size to maintain the adjacent spinous processes in a predetermined alignment.

In one embodiment, the spacer is constructed of a flexible material that is sized to fit within the opening in the patient and be delivered to the application point. Biomaterial is then fed into the spacer to expand the size to the desired dimensions. In another embodiment, the spacer is constructed of a material that is sized to fit within the opening in the patient and be delivered to the application point. Once at this point, the spacer expands to the desired size and dimensions.

In one embodiment, a conduit is inserted within the patient for delivering the spacer to the application point. The conduit is hollow to provide a pathway for delivering the spacer. In the embodiment using a biomaterial to expand the spacer, the hollow conduit may also provide a means for delivering the biomaterial to the interior of the spacer.

In one embodiment, the conduit is comprised of one or more conduit sections of increasing size. A first conduit section is placed within the patient to form a small opening, and then increasingly larger conduit sections are inserted within the opening until the opening is the desired size. Any number of different conduit sections may be used in this process. In one embodiment, each of the conduit sections has a length such that a first end can be positioned at the application point, and the second end remains outside of the patient where it can be handled by medical personal.

DETAILED DESCRIPTION

Figure 1:
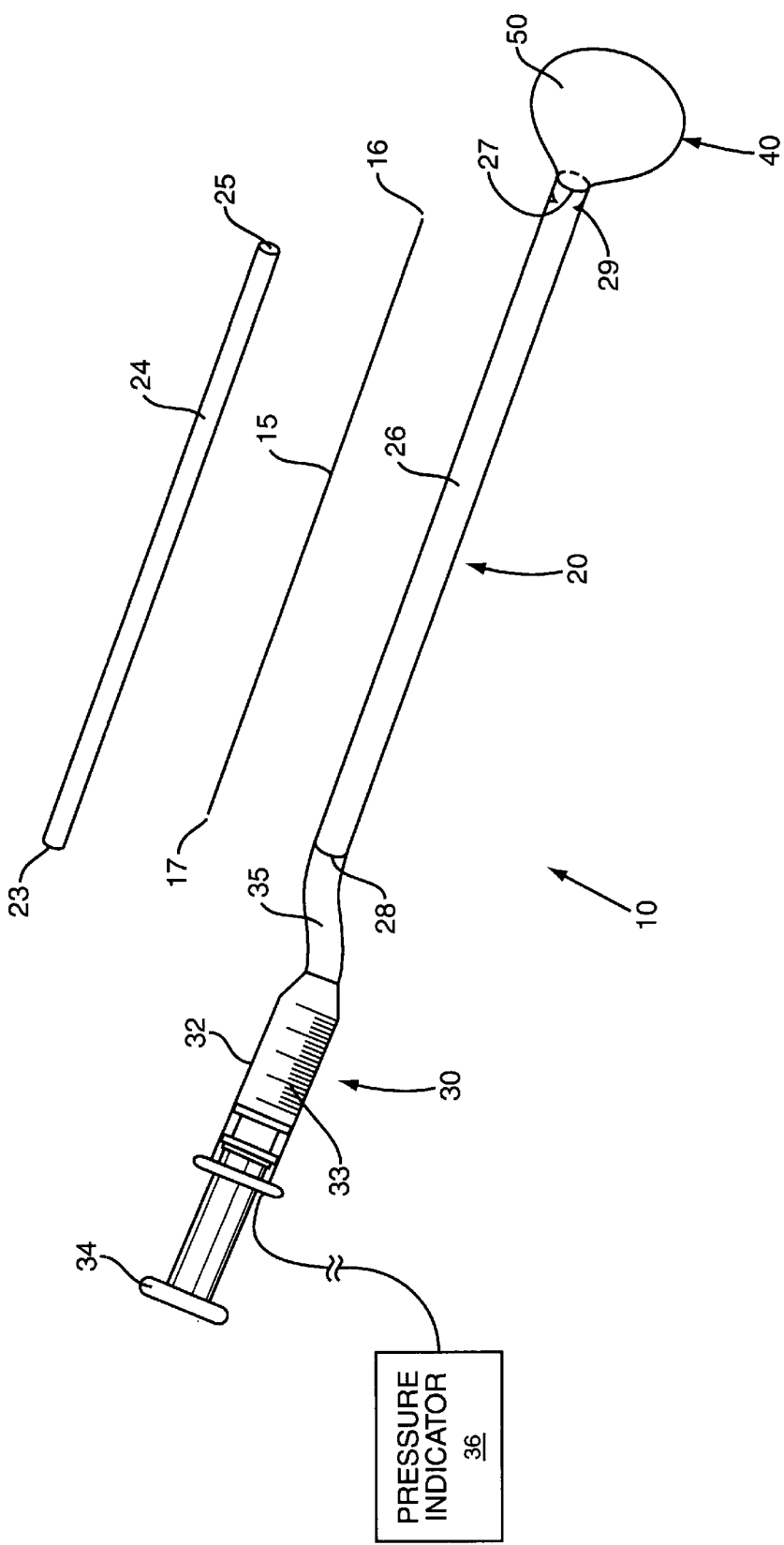
FIG. 1 is a perspective view illustrating one embodiment of the device with a rod and first and second conduit sections.

FIG. 1 illustrates one embodiment of the present invention, generally illustrated as 10, that comprises a conduit 20, delivery device 30, and a spacer 40. The conduit 20 forms a passage through which biomaterial 50 is moved from the delivery device 30 to the spacer 40 during the procedure as will be described in more detail below. The delivery device 30 functions to move the biomaterial 50 through the conduit 20 and into the spacer 40. The spacer 40 is constructed of an expandable material and positioned at the outlet end 27 of the final conduit section 26. The spacer 40 is removed from the final conduit section 26 and permanently positioned within the patient.

The conduit 20 positions the spacer 40 at the desired position within the patient and serves as a passageway for moving the biomaterial 50 from the delivery device 30. In one embodiment as illustrated in FIG. 1, the conduit 20 includes a rod 15, and one or more conduit sections 24, 26. Each additional conduit section 24, 26 has an increased size for dilating the size of the opening within the patient. The present invention may include any number of conduit sections to expand the opening to the desired size. For ease of reference, conduit section 26 illustrates a final conduit section inserted into the patient that expands the opening to the furthest extent. In another embodiment, final conduit section 26 is the first and only section inserted into the patient.

In the embodiment illustrated in FIG. 1, the rod 15, having a first end 16 and a second end 17, is initially inserted into the patient. The rod 15 has a length such that the first end 16 can be inserted into the patient and positioned at the injury while the second end 17 remains outside of the patient. It is understood that the rod 15 may have a variety of lengths depending upon the position of the application point and the size of the patient. First end 16 may further include a sharpened tip to ease the insertion process into the patient.

Second end 17 may include a grip (not illustrated) or other like holding device to assist the physician in grasping and manipulating the rod 15. In one embodiment, rod 15 is a solid member. In another embodiment, rod 15 is hollow, such as a needle.

Conduit sections 24, 26 are inserted after the rod 15 to increase the size of the opening in the patient. Each conduit section 24, 26 has an interior area to be inserted over the previously inserted conduit section. By way of example, conduit section 24 has an interior area to receive rod 15, and final conduit section 26 has an interior area to receive conduit section 24. Therefore, after the rod 15 is inserted, conduit section 24 is inserted over the rod 15 to increase the opening a first amount and then final conduit section 26 is inserted over conduit section 24 to again increase the opening. The increase in size of each succeeding conduit section may vary depending upon the desired results. Additionally, it is understood that this embodiment of the present invention may include any number of conduit sections to gradually increase the size of the opening to the desired amount.

In one embodiment, each conduit section 24, 26 includes openings at the first and second ends. In this embodiment, and using conduit section 24 as an example, conduit 24 is hollow to receive the previously-inserted section and allow it to pass within and be removed from the patient. The conduit section 24 is hollow along the entire length and may have varying cross-sectional areas throughout the length. As with the rod 15, a grip (not illustrated) may be mounted on the second ends of each section to assist the medical personnel in grasping and manipulating the conduit section.

The inner area of the final conduit section 26 may vary depending upon the specific application. In one embodiment, the final conduit section 26 has an inner opening of between about 2 mm to about 6 mm, and in another embodiment, between about 3 mm to about 5 mm.

A cutter 29 may be positioned within the final conduit section 26 to cut and detach the spacer 40. In one embodiment, cutter 29 is comprised of two circular rotating blades that have offset rotational centers. Each blade rotates about its rotational center and together combine to cut the spacer 40.

In one embodiment, each member of the conduit 20 is constructed of a material that is visible with an X-ray or other diagnostic equipment to allow the medical personnel to view the procedure and ensure the sections are being placed correctly within the patient. This provides for the physician to view the procedure via X-ray or other like equipment. Otherwise, an incision in the patient or other more invasive means would be required to allow the physician to visually observe the procedure.

Delivery device 30 functions to move biomaterial 50 through the conduit 20 and into the spacer 40. A variety of delivery devices 30 may be used to accomplish this function. In the embodiment illustrated in FIG. 1, a syringe-like device comprises a body 32 for holding the biomaterial 50 and a plunger 34 for forcing the biomaterial 50 through the conduit 20 and into the spacer 40. Delivery device 30 may further include an indicator to determine the amount of material fed to the spacer. In the embodiment illustrated in FIG. 1, a scale 33 is printed on the body 32 to visually determine the amount of expelled biomaterial 50. A pressure indicator 36 may also be included on the delivery device 30 to indicate the pressure at which the biomaterial is being fed into the spacer 40.

In another embodiment (not illustrated), biomaterial 50 is stored in one or more remotely-located storage locations. A device (not illustrated) moves the biomaterial from the storage locations either into the delivery device 30 for delivery or into the conduit 26 and spacer 40. The device may be equipped with an activation switch, as well as volume indicator to allow the physician to control the amount and rate of biomaterial 50.

An intermediate member 35 may be positioned between the delivery device 30 and conduit 20. In one embodiment, intermediate member 35 is a flexible hose that isolates the conduit 20 so any movement of the delivery device 30 is not transferred to the patient. Intermediate member 35 also makes the procedure more ergonomically convenient for the medical personnel by providing flexibility for positioning the personnel relative to the patient during the procedure.

Various types and sizes of spacers 40 may be used in the present invention. In each embodiment, spacer 40 has a first form that allows it to be delivered into the patient in a minimally-invasive manner to the application point. The spacer 40 expands to an enlarged second form at the application point inside the patient.

In one embodiment, spacer 40 is constructed of a flexible material for receiving the biomaterial 50. The spacer 40 enlarges as the biomaterial is inserted and may expanded to any desired size. In another embodiment, spacer is constructed of a material that expands once within the patient. The spacer has a reduced first form to fit through the opening prior to expanding at the application point.

Spacer 40 may be constructed to include a single unitary compartment having an outer wall, or may include a number of separate compartments having interior dividers. Spacer 40 may comprise a single layer, or may include two or more overlapping layers. The spacer 40 may be constructed of a variety of expandable, biocompatible materials including, but not limited to, polyolefin copolymers, polyethylene, polycarbonate, and polyethylene terephthalate. The materials may further include integrated fibers to further strengthen the spacer 40. The spacer 40 may further be constructed of a radio opaque material to be seen on an X-ray by the physician during the procedure.

Figure 2A:
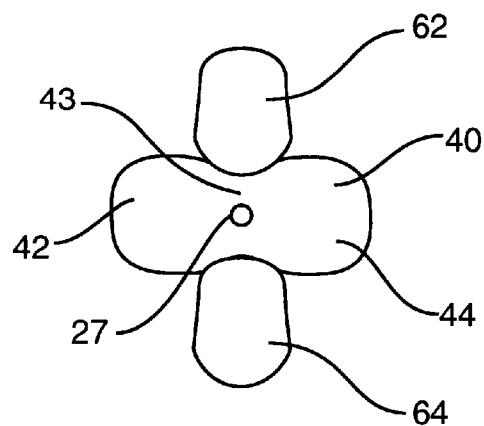
FIG. 2A is a posterior view illustrating one embodiment of the spacer positioned between adjacent spinous processes.
Figure 2B:
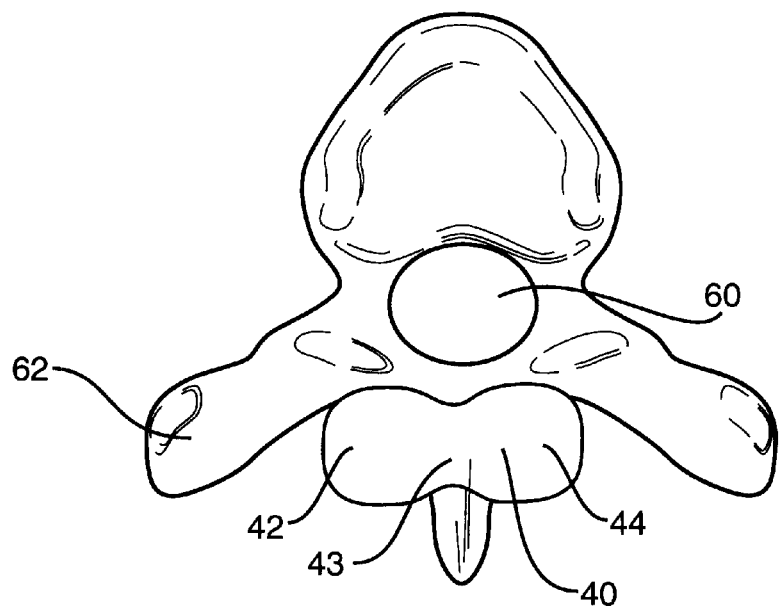
FIG. 2B is a top view of the embodiment illustrated in FIG. 2A illustrating the spacer.

FIG. 2A illustrates one embodiment of a spacer 40 positioned between two adjacent spinous processes 62, 64. In this embodiment, spacer 40 has an hourglass shape that includes enlarged ends 42, 44 and a narrow middle section 43. The shape is configured such that the middle section 43 maintains a predetermined spacing between adjacent spinous processes 62, 64, and the lateral portions 42, 44 are configured to maintain the positioning of the spacer 40. FIG. 2B illustrates the positioning of the spacer 40 along the spinous process 62. Spacer 40 may have a variety of shapes and sizes depending upon the desired implementation, and may be positioned along the spinous processes 62, 64 in a variety of positions.

The spacer 40 has a size and shape in the unexpanded state to be inserted into the patient through the opening that is created by the conduit 20. In one embodiment, the unexpanded spacer 40 is mounted within the final conduit 26 and includes an opening aligned with the hollow interior of the final conduit 26. The biomaterial 50 is delivered through the final conduit 26 and into the spacer 40. Biomaterial 50 is delivered into the spacer until the desired shape and size is obtained and cutters 29 cut the spacer 40 from the conduit 20. The portion of the spacer 40 cut from the filled section remains within the conduit 20 where it is removed from the patient. An optional seal or tie may be placed on the spacer 40 to close the opening formed during the cutting process. In one embodiment, a seal is placed around the interior or exterior of the final conduit section first end 27. After cutting, the seal or tie is mounted on the spacer 40 to close the opening. In another embodiment, the cut open remains open as the biomaterial cures and does not leak from the spacer 40. Additionally, the biomaterial is safe to the patient and it is not necessary to seal it within the spacer 40.

In another embodiment, the unexpanded spacer 40 is inserted into the final conduit section 26 through the second end 28. The movement of the biomaterial 50 forces the unexpanded spacer through the final conduit section 26 and into the patient. Once in the patient and out of the final conduit section 26, the spacer expands. In one embodiment, expansion results by receiving the inserted biomaterial 50. In another embodiment, the spacer 40 is constructed of a material that expands when positioned within the patient.

Biomaterial 50 should have an initial viscosity to be moved from the delivery device 30, through the conduit 20, and into the spacer 40. Once within the spacer 40, biomaterial should cure, meaning that it progresses from an initial flowable form during delivery to a more permanent form for final use in vivo. In one example, permanent form comprises a substantially rigid shape capable of maintaining a predetermined spacing between internal body components, such as bone. Biomaterial 50 may be a single component supplied from the delivery device 30, or may include two or more different components that are mixed together prior to or during delivery. The biomaterial may further be homogeneous with the same chemical and physical properties throughout, or heterogeneous. A variety of biomaterials 50 may be used in the present invention and may include polyvinyl chlorides, polyethylenes, styrenic resins, polypropylene, thermoplastic polyesters, thermoplastic elastomers, polycarbonates, acrylonitrile-butadiene-styrene resins, acrylics, plyurethanes, nylons, styrene acrylonitriles, and cellulosics. These materials are described in U.S. Pat. No. 5,888,220, herein incorporated by reference in its entirety. Biomaterial may further include an opaque additive that will be visible on an X-ray. One type of additive includes barium sulfate.

FIGS. 3–6 illustrate the steps of inserting a spacer 40 within a patient according to one embodiment of the present invention. Vertebrae become misaligned resulting in the spinal canal 60 being pinched, thereby causing pain, numbness in the lower extremities, and other symptoms. To alleviate this injury, the vertebrae may be adjusted or realigned to stop the pinching. FIGS. 3–6 feature the spacer 40 being inserted between adjacent spinous processes 62, 64 which extend posteriorly from the vertebrae.

Figure 3:
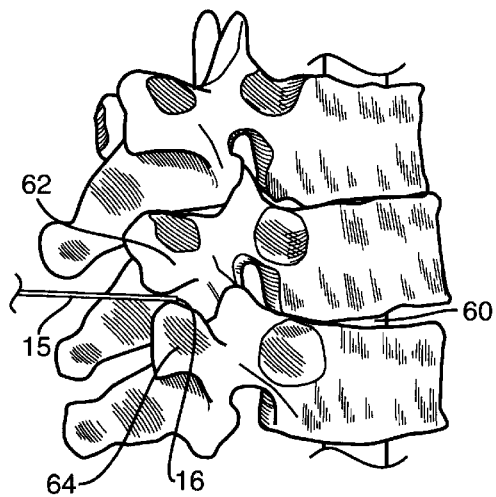
FIG. 3 is a side view of one embodiment illustrating a rod inserted between two adjacent spinous processes.

FIG. 3 illustrates the initial step of one embodiment of inserting the rod 15 into the patient until the first end 16 is positioned at the application point. In this embodiment, first end 16 is positioned between the misaligned adjacent spinous processes 62, 64. The patient is positioned on their side or in the prone position and the physician visually observes the placement of the rod 15 through X-ray or other diagnostic equipment. The rod 15 is inserted and normally only requires the use of a local anesthesia.

Figure 4:
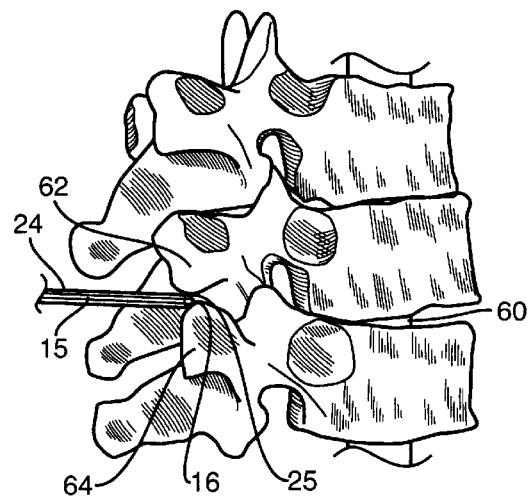
FIG. 4 is a side view of the one embodiment illustrating a conduit section positioned around the rod.

FIG. 4 illustrates inserting a first conduit section 24 over the rod 15. The outer end of the rod 15 is placed within the opening in the conduit section first end 25 and the conduit section 24 is slid down the rod 15 until the first end 25 is positioned at the point proximate to the rod first end 16. The rod 15 may than be removed leaving only the conduit section 24 in the patient.

Figure 5:
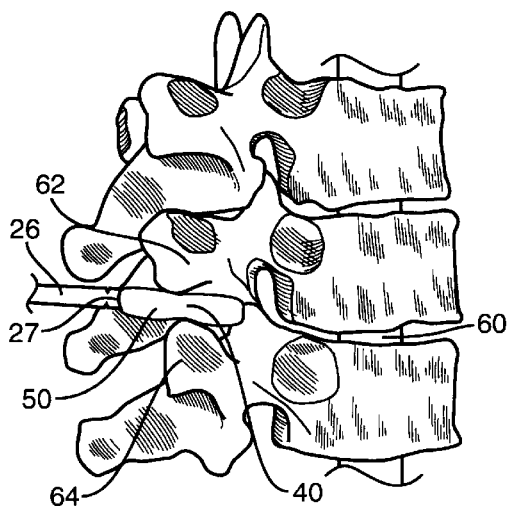
FIG. 5 is a side view of the one embodiment illustrating a spacer extending outward from the end of a final conduit section and being expanded by a biomaterial being inserted within.

In this embodiment, one or more additional conduit sections may be inserted over the conduit section 24 depending upon the required size of the opening. A final conduit section 26 is inserted with a first end 27 positioned at the application point. At this stage, spacer 40 is deployed from the first end 27 as biomaterial 50 is pumped from the delivery device 30, through the conduit section 26, and into the spacer 40 as illustrated in FIG. 5. The size of the spacer 40 increases as the biomaterial enters. The physician can observe the procedure through the equipment to monitor the placement and size of the spacer 40 and the corresponding realignment of the spinous processes 62, 64. The physician additionally monitors the volume scale 33 on the delivery device 30 and/or the pressure indicator 36.

Upon complete deployment, the spacer 40 is removed from the final conduit section 26. In one embodiment, the biomaterial 50 cures in a predetermined amount of time prior to the removal of the final conduit section 26. In another embodiment, the spacer 40 is removed from the final conduit section 26 prior to being cured. The opening formed in the spacer 40 when cut from the final conduit section 26 may be sealed to completely enclose the biomaterial, or may remain unsealed as the open/exposed biomaterial cures to form a seal. After removing the spacer 40, the final conduit section 26 is removed from the patient. As illustrated in the progression of FIGS. 3–6, the adjacent spinous processes 62, 64 are aligned by the expanded spacer 40 thus reducing or eliminating the pinching of the spinal column 60.

Figure 6:
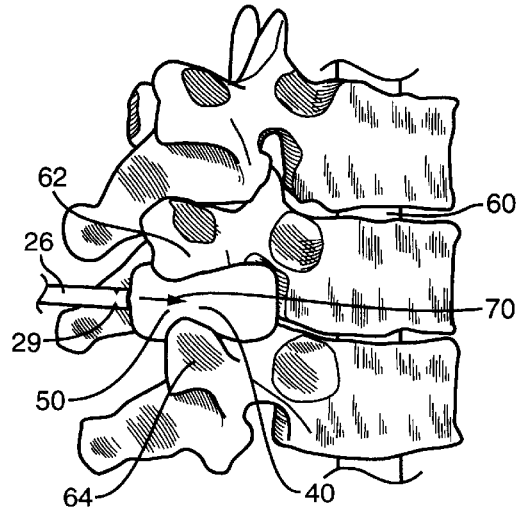
FIG. 6 is a side view of the one embodiment illustrating another progression with the spacer expanded to full size and being removed from the end of the final conduit section.

The spacer 40 is positioned within the patient relative to the position of the first end of the final conduit section 27. In one embodiment as illustrated in FIGS. 5 and 6, the spacer 40 expands linearly outward from the conduit end 27 in the direction indicated by arrow 70 an amount proportional to the amount of biomaterial fed into the spacer 40. In this embodiment, the amount of expansion extends beyond the insertion point of the conduit 26. By way of example, when the conduit is inserted into the patient at a starting point, the final position of the spacer 40 within the patient will be the starting point+expansion. The force of the biomaterial expanding the spacer 40 is such that it is not necessary that tissue be removed from the patient.

In another embodiment as illustrated in FIG. 2, spacer 40 extends outward from the final conduit end 27 in a lateral direction with respect to the longitudinal axis of the conduit 20. The expansion of the spacer 40 within the patient is a function of the spacer shape and the amount of expansion of the spacer 40. Therefore, positioning the final conduit end 27 is important for determining the final position of the spacer 40. The spacer 40 may be constructed to expand in any direction relative to the conduit 20 and may form any type of predetermined shape.

In one embodiment with the final conduit section 26 having an inner opening of between about 2 mm to about 6 mm, the opening into the patient is only slightly larger than the size of the conduit opening, or between about 4 mm to about 8 mm. Inherent with the small opening, the patient does not lose a noticeable amount of blood during the procedure. Additionally, the procedure can be performed in a flouro-suite as opposed to a more expensive operating room, can usually be accomplished using local anesthesia and conscious sedation, and does not require a prolonged hospital stay during patient recovery.

In another embodiment of the present invention, conduit 20 comprises a single member. The final conduit section 26 is the only conduit member inserted into the patient. The procedure comprises a single step of inserting the conduit section 26 and moving biomaterial into the spacer 40. In this embodiment, there is no initial rod 15 or preliminary conduit sections 24.

The spacer 40 may distract the area within the patient. In one embodiment, deployment of the spacer 40 is initially performed by forcing pressurized fluid into the spacer to expand the spacer 40. After expansion, biomaterial 50 is moved via the delivery device 30, through the conduit section 26, and into the spacer 40. This embodiment may further include a vent leading from the spacer out of the conduit section to remove the liquid from the interior of the spacer as the biomaterial is being inserted.

In another embodiment, the area within the patient has already been distracted and the spacer 40 is placed within the area. The space may be created in a number of different manners, including a balloon catheter which is inserted into the position, inflated with a suitable gas such as nitrogen or carbon dioxide to expand the balloon and create a desired opening, deflated, and then removed. One type of balloon catheter is the KyphX Inflatable Bone Tamp marketed by Kyphon. After removal, the spacer 40 can be inserted using the processes of the present invention.

The present invention may be carried out in other specific ways than those herein set forth without departing from the scope and essential characteristics of the invention. In one embodiment, a vent (not illustrated) is inserted within the spacer 40 during expansion and is a passage for gas to exit the patient. In one embodiment, the spacer 40 is a balloon similar to those presently used for angioplasty. In another embodiment, the opening is used for introducing the spacer 40 into the patient, and biomaterial 50 is introduced into the spacer 40 through a different pathway, such as a needle inserted into the patient. In one embodiment, the system and method are used for positioning adjacent spinous processes. However, the present invention may also be applicable to space other bodily tissue. The present embodiments are, therefore, to be considered in all respects as illustrative and not restrictive, and all changes coming within the meaning and equivalency range of the appended claims are intended to be embraced therein.

What is claimed is:

1. A method of positioning adjacent spinous processes, comprising:
   inserting a conduit to a predetermined position between the adjacent spinous processes;
   inserting a spacer in a first form through the conduit to the predetermined position; and
   changing the spacer to a second form that maintains the adjacent spinous processes in a predetermined alignment, the second form having an expanded size relative to the first form.

2. The method of claim 1, wherein changing the spacer to a second form comprises inserting a biomaterial within the spacer and expanding the spacer to the expanded size.

3. The method of claim 1, wherein changing the spacer to a second form comprises the spacer expanding to a predetermined size that is larger than the first form.

4. A method of placing a spacer between adjacent spinous processes of a patient, comprising:
   inserting a conduit into the patient such that a first end is positioned at an application point between the adjacent spinous processes;
   attaching a delivery device to the conduit; and
   delivering biomaterial from the delivery device through the conduit and into a spacer positioned within the conduit, the spacer expanding beyond the end of the conduit and into the patient at the application point.

5. The method of claim 4, wherein inserting the conduit into the patient such that the first end is positioned at the application point between the adjacent spinous processes comprises positioning the first end at a point that is an outer edge of a final spacer position within the patient.

6. The method of claim 4, wherein inserting the conduit into the patient such that the first end is positioned between the adjacent spinous processes comprises positioning the first end at a point between the adjacent spinous processes that is a middle of a final spacer position within the patient.

7. The method of claim 4, wherein the conduit has a length such that when the first end is positioned at the application point, a second end remains outside of the patient.

8. The method of claim 4, wherein inserting the conduit into the patient comprises inserting a rod into the patient with a first rod end positioned proximate to the application point followed by inserting at least one conduit section over the rod, the at least one conduit section being larger than the rod such that the at least one conduit section can be slid over the rod to position an end of said conduit section proximate to the application point.

9. The method of claim 4, further comprising forming an opening ranging in size from between about 3 mm to about 8 mm in the patient.

10. The method of claim 4, wherein the spacer has an hourglass shape with enlarged end sections being placed on the exterior of the adjacent spinous processes and a middle section being positioned between the adjacent spinous processes after delivery of the biomaterial.

11. A minimally-invasive method of placing a spacer within a patient for spacing bodily tissue comprising:
   creating an opening within the patient that extends between the skin and an application point between adjacent spinous processes, the opening ranging in size from between about 3 mm to about 8 mm;
   delivering a spacer through the opening to the application point, the spacer having a first size to be delivered through the opening; and
   expanding the spacer at the application point to a second size, the second size being larger than the opening.

12. The method of claim 11, further including viewing the spacer within the patient using diagnostic equipment and stopping the expansion of the spacer when it visually appears to have enlarged to a desired size.

13. The method of claim 11, wherein the spacer is constructed of a flexible material sized to be delivered through the opening and is expanded by delivering biomaterial into an interior of the spacer.

14. The method of claim 13, wherein the biomaterial comprises barium sulfate.

15. The method of claim 13, wherein the biomaterial is in a viscous form when delivered through the opening to the interior of the spacer.

16. The method of claim 15, further comprising determining a volume of the biomaterial fed from a delivery device when the spacer has expanded to the second size.

17. A method of inserting a spacer within a patient between adjacent spinous processes in a minimally invasive manner, the method comprising the steps of:
   inserting a conduit into the patient and positioning a first end of the conduit between the adjacent spinous processes with a second end of the conduit being outside of the patient, the conduit comprising a hollow interior;
   delivering a spacer through the hollow interior of the conduit to a position within the patient between the adjacent spinous processes; and
   delivering biomaterial through the conduit and into the spacer to expand the spacer.

18. The method of claim 17, wherein the spacer distracts the space between the adjacent spinous processes within the patient.

19. The method of claim 17, further comprising detaching the spacer from the conduit after expanding the spacer to a desired size.

20. The method of claim 17, further comprising distracting the spinous process prior to delivering the spacer between the spinous processes.

21. A method of relieving pain due to spinal stenosis, said method comprising the steps of:

positioning a spacer between adjacent spinous processes of the spinal column by forming an opening in the patient no larger than about 8 mm in diameter; and expanding the spacer to alter the position of each of the adjacent spinous processes to increase the volume of the spinal canal.

22. A method of placing a spacer within a patient for spacing apart bodily tissue without previously resecting tissue, the method comprising the steps of:

inserting a conduit into the patient with a conduit first end positioned between adjacent spinous processes;

moving biomaterial into the conduit;

forcing the biomaterial into a spacer located at the conduit first end and expanding the size of the spacer; and detaching the spacer from the conduit.

23. An apparatus for maintaining a predetermined spacing between adjacent spinous processes comprising a spacer changeable between a first form and a predetermined second form, the first form having a reduced size to be inserted between the adjacent spinous processes in a minimally invasive manner, the second form configured to have an enlarged size with an hourglass shape that securely positions the spacer between the adjacent spinous processes to maintain the predetermined spacing.

24. A system for positioning adjacent spinous processes comprising:

a conduit insertable to a predetermined position relative to the adjacent spinous processes; and a spacer having a body configured to be changeable from a first form to a predetermined second form, the first form sized to be delivered through the conduit, and the second form sized to maintain the adjacent spinous processes in a predetermined position, the second form comprises a first end section having a first height, a second end section having a second height, and a middle section having a third height, wherein the third height is less than either of the first height and the second height.

25. The system of claim 24, further comprising a biomaterial having a first state and a second state, wherein the first state is suitable for delivery through the conduit and into the body of the spacer, and wherein the second state is substantially elastic to prevent compression of a space between the adjacent spinous processes.

26. The system of claim 24, wherein the second form is larger than the first form.

27. A system for positioning adjacent spinous processes, comprising:

a spacer having a first shape and a predetermined second shape, wherein the first shape has a first size and the predetermined second shape has a second size substantially larger than the first size, wherein the predetermined second shape is configured to support the adjacent spinous processes and has enlarged ends and a narrow middle section; and wherein the spacer comprises a material configurable into the predetermined second shape.

28. The system of claim 27 the material has a first state and a second state, wherein the first state comprises a substantially flowable fluid, and wherein the second state comprises a substantially rigid structural material.

29. The system of claim 27, wherein the material has a first state and a second state, wherein the first state comprises an unexpanded form of the material having a first volume, and wherein the second state comprises an expanded form of the material having a second volume substantially greater than the first volume.

30. The system of claim 27, wherein the predetermined second shape comprises a first end section having a first height, a second end section having a second height, and a middle section having a third height, wherein the third height is less than either of the first height and the second height.

* * * * *